United States Patent [19]

O'Neill

[11] Patent Number: 4,986,279
[45] Date of Patent: Jan. 22, 1991

[54] LOCALIZATION NEEDLE ASSEMBLY WITH REINFORCED NEEDLE ASSEMBLY

[75] Inventor: William J. O'Neill, Gainesville, Fla.

[73] Assignee: National-Standard Company, Niles, Mich.

[21] Appl. No.: 317,607

[22] Filed: Mar. 1, 1989

[51] Int. Cl.⁵ .............................................. A61B 10/00
[52] U.S. Cl. ...................................... 128/754; 604/164
[58] Field of Search ................... 128/330, 340, 329 R, 128/339, 751, 753, 754; 604/164–169

[56] References Cited

U.S. PATENT DOCUMENTS

| | | | |
|---|---|---|---|
| 3,612,058 | 10/1971 | Ackermann | 128/772 |
| 3,618,613 | 11/1971 | Schulte | 604/282 |
| 4,215,703 | 8/1980 | Willson | 128/772 |
| 4,516,972 | 5/1985 | Samson | 604/282 |
| 4,579,127 | 4/1986 | Haacke | 128/772 |
| 4,592,356 | 6/1986 | Gutierrez | 606/185 |
| 4,619,274 | 10/1986 | Morrison | 128/772 |
| 4,636,200 | 1/1987 | Vaillancourt | 604/170 |
| 4,655,771 | 4/1987 | Wallsten | 623/1 |
| 4,676,249 | 6/1987 | Arenas et al. | 128/657 |
| 4,682,607 | 7/1987 | Vaillancourt | 128/772 |
| 4,721,117 | 1/1988 | Mar et al. | 128/772 |
| 4,724,846 | 2/1988 | Evans, III | 128/772 |
| 4,737,153 | 4/1988 | Shimamura et al. | 604/282 |
| 4,756,708 | 7/1988 | Martin | 128/760 |
| 4,774,948 | 10/1988 | Markham | 606/185 |
| 4,790,329 | 12/1988 | Simon | 128/754 X |
| 4,799,495 | 1/1989 | Hawkins et al. | 128/754 |

OTHER PUBLICATIONS

Sales Brochure entitled, "N–S Strand & Cable", 12/86, pp. 1-5, National Standard Specialty Products.

Primary Examiner—Robert A. Hafer
Assistant Examiner—Lynda M. Cofsky
Attorney, Agent, or Firm—Emrich & Dithmar

[57] ABSTRACT

A localization needle assembly includes an outer tubular cannula and a reinforced needle structure slidably mounted for movement within the outer cannula between extended and retracted portions, the needle structure defining a rearwardly extending barb which is contained within the outer cannula when the inner needle is extended while the surgeon locates a lesion. When the inner needle is retracted, the barb is deployed through an opening in the sidewall of the outer cannula for anchoring the localization needle assembly in body tissue in the proximity of the lesion.

28 Claims, 3 Drawing Sheets

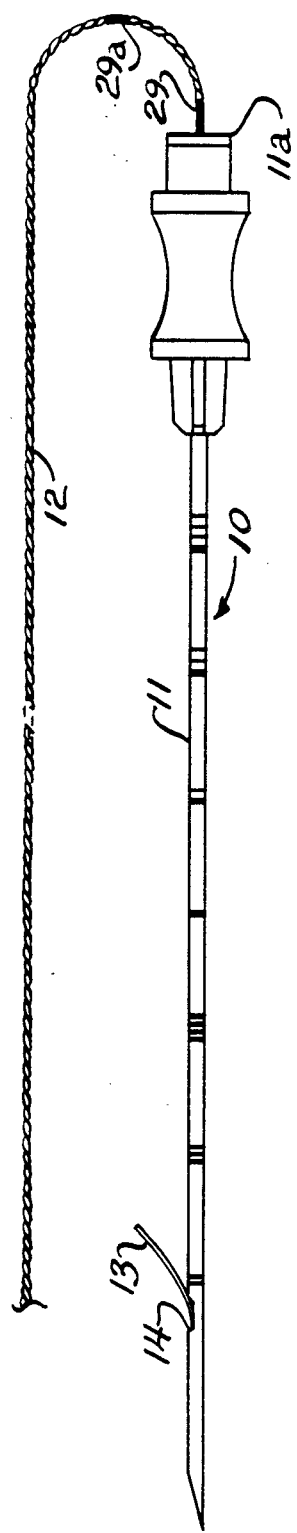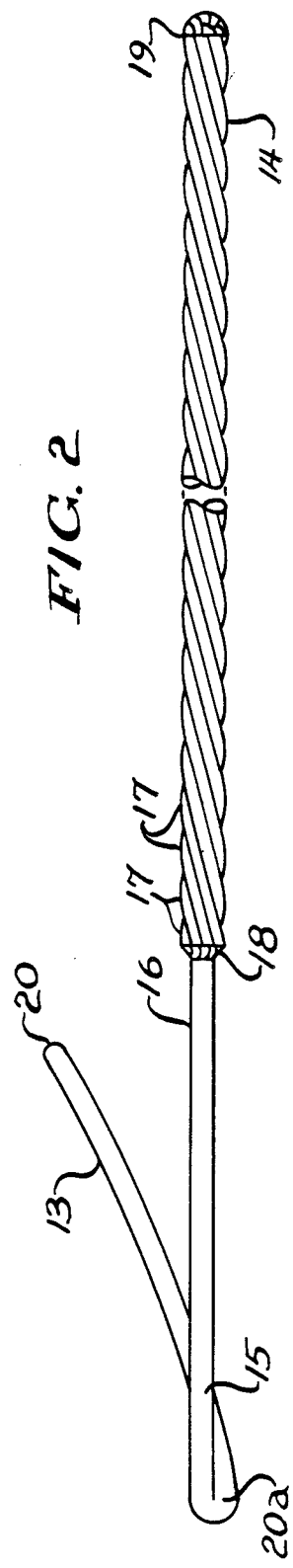

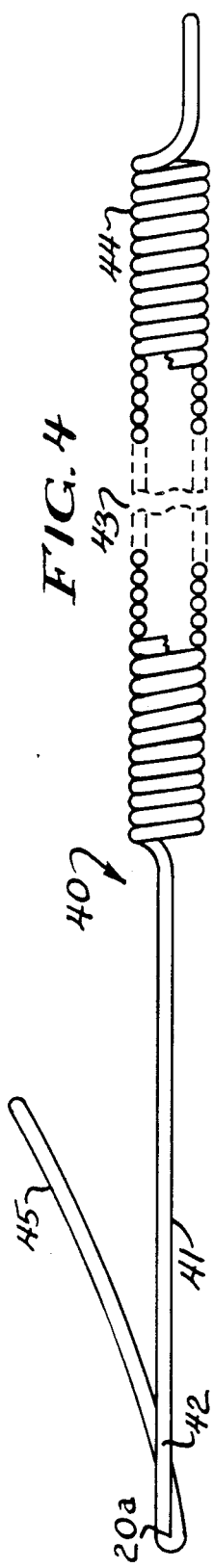
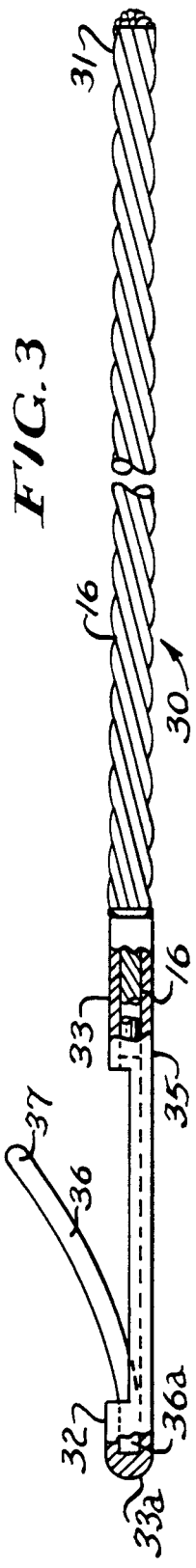
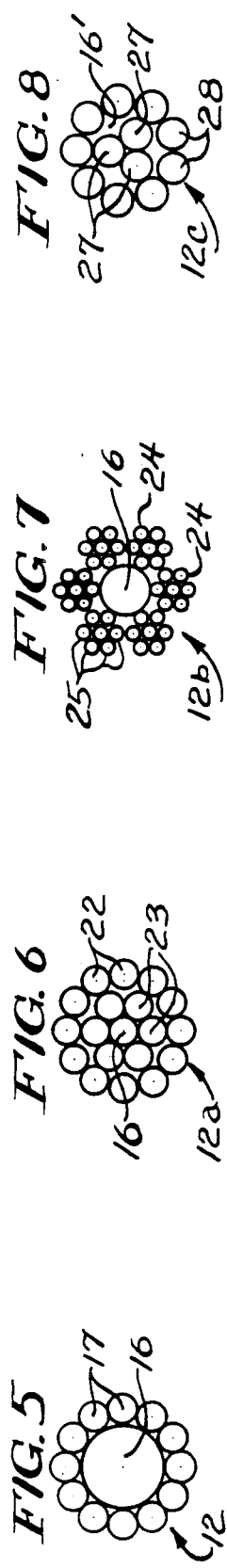
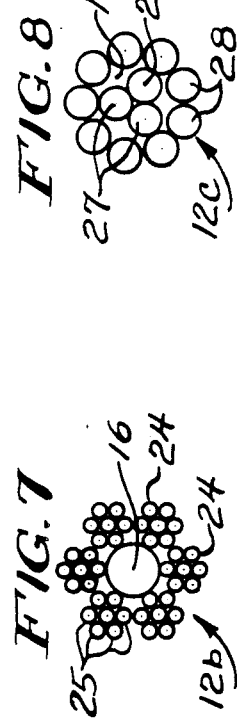
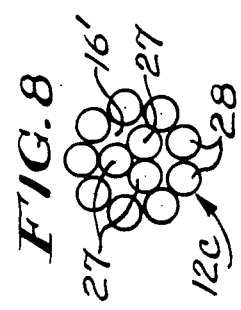
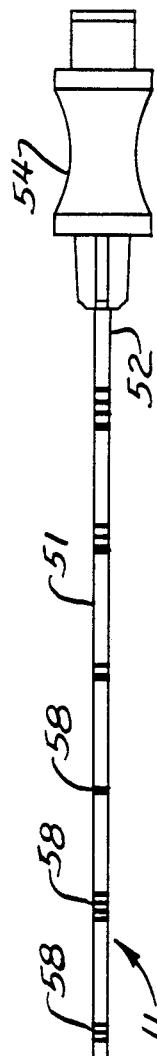
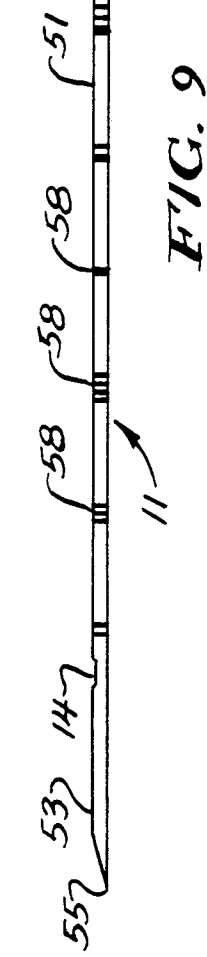

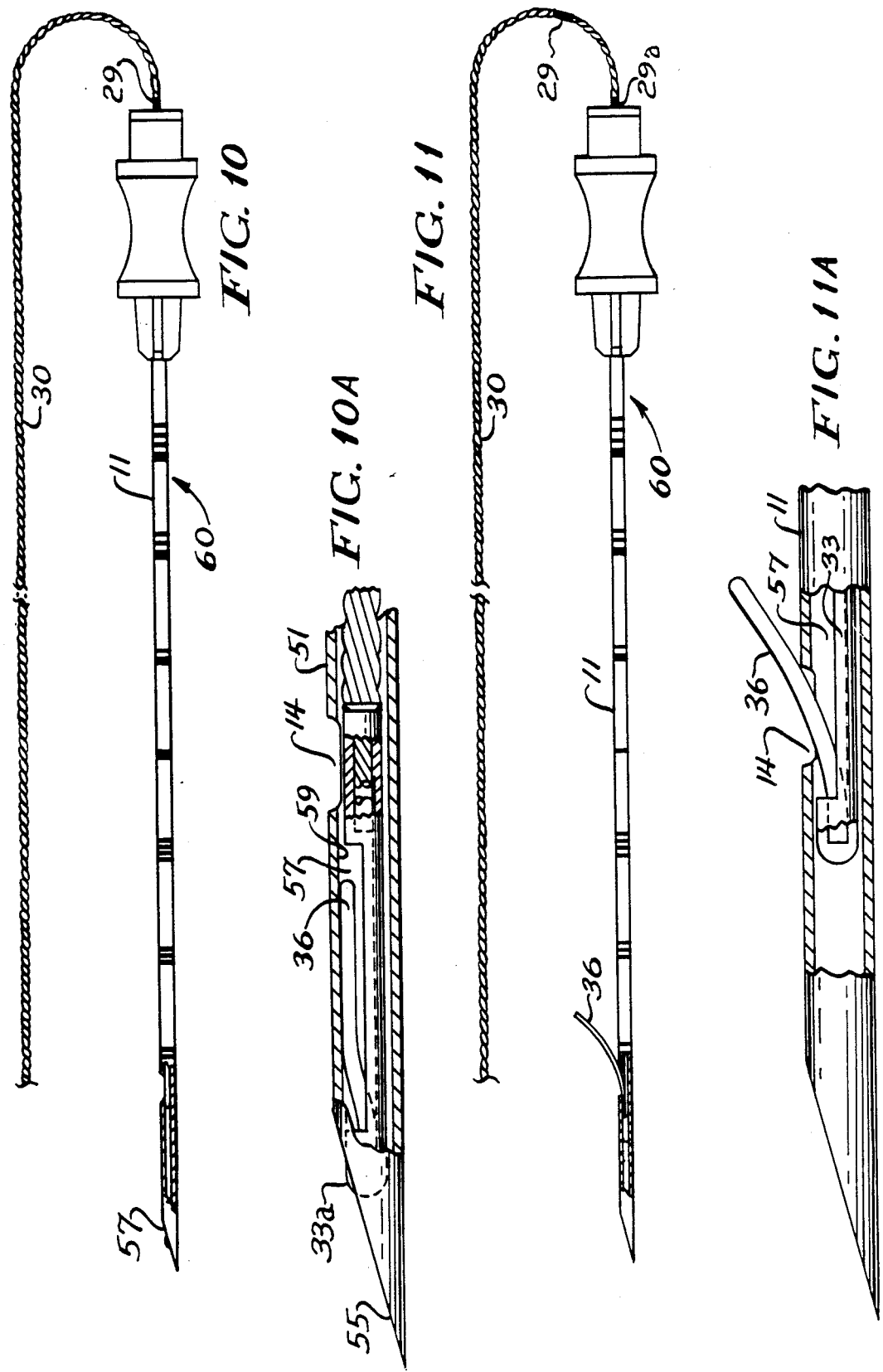

LOCALIZATION NEEDLE ASSEMBLY WITH REINFORCED NEEDLE ASSEMBLY

BACKGROUND OF THE INVENTION

The present invention relates to a novel localization needle assembly which may be readily inserted into and anchored within body tissue to identify to the surgeon the location of nonpalpable lesions.

Various localization needle systems have been proposed to aid the surgeon in locating nonpalpable lesions within the breast. In one system commonly referred to as a needle and hook-wire system, a hypodermic needle is initially placed into the breast to locate the breast lesion When the needle is properly placed, a stainless steel wire having a hairpin hooked-end portion is slid through the needle wherein the hooked hairpin-end portion exits from the needle to engage the body tissue to retain the needle adjacent to or at the breast lesion The introducing needle is withdrawn over the wire and the wire is anchored to the tissue and the patient is taken to surgery. The wire permits the surgeon to know where the lesion lies within the breast tissue.

However, this needle and wire-hook arrangement possesses several disadvantages. For example, during mammographic filming of the breast lesion and the location of the needle within the breast, the breast is compressed and this can cause the needle to move or be displaced with respect to the breast lesion. Additionally, after the hairpin-end hook wire has been inserted through the needle and expanded to anchor the needle/hook-wire apparatus in place, an additional set of mammograms is required to verify the positioning of the needle within the breast tissue. If the position is incorrect, the hooked wire cannot be easily removed and forceful removal results in considerable damage to the tissue as well as the fact that the ultimate removal of the hook-wire from the breast causes undesirable tearing and damage to the breast tissue.

Another needle/wire device and technique includes a curved-end wire which is made of a tough pseudo-elastic alloy which possesses a memory. A needle containing a wire having a J-shaped hook on the end is inserted into the breast and advanced to identify the location of the breast lesion. The wire is then advanced inwardly such that the curved hooked end engages the body tissue to immobilize the needle during mammography imaging to insure that the needle is correctly positioned at or adjacent the breast lesion. The needle and hook device can be relatively easily displaced if traction or pressure is applied to the breast during transport of the patient or during surgery. Thus, actual migration of the hook-wire device in the breast tissue occurs during surgery and movement of the patient to surgery.

Both of those systems employ a single wire needle for anchoring the localization needle assembly to body tissue. The wire needle must be flexible and pliable to allow easy handling and fastening of the proximal end of the wire outside of the patient's body and to resist the risk of unintended penetration or migration. However, because the needle wire must be sufficiently large so as to resist accidental transection by the surgeon during excision, this limits the amount of flexibility and pliability obtainable for known needle anchoring arrangements which employ a single wire.

SUMMARY OF THE INVENTION

It is therefore an object of the present invention to provide a new and improved localization needle assembly for use in locating and pinpointing lesions within a body.

Another object of the present invention is a novel localization needle assembly which may be readily positioned and locked within body tissue to precisely locate and pinpoint lesions for subsequent surgical removal or biopsy.

Another object of the present invention is a novel localization needle assembly which includes a retractable anchoring means located within a cannula and which is adapted to be extended outwardly from the side wall of the cannula to lock and anchor the localization needle assembly to the body tissue to precisely locate lesions for subsequent surgical removal.

Still another object of the present invention is a needle structure for a localization needle assembly which is characterized by greater flexibility and pliability than that for known comparable sized needles and which resists accidental transection.

These and other objects are achieved by the present invention which provides a localization needle assembly for pinpointing lesions within body tissue, including in combination an outer tubular cannula member having a distal end and a proximal end with said cannula member having an opening predeterminedly located from said distal end, and an elongated inner needle structure having a distal end and a proximal end. The needle structure has a linear portion at its distal end and a reinforced portion intermediate its proximal and distal ends. The linear portion of the needle structure has anchoring means including a barb. The needle structure is slidably mounted for movement within said the cannula member between a first position and a second position, the barb extending towards the opening in the outer cannula member when the needle structure is in the first position and the barb being moved outward of the outer cannula member through the opening predeterminedly located from the distal end of the outer cannula member to engage body tissue when the needle structure is moved to the second position to anchor the localization needle assembly to body tissue.

With these and further objects of the present invention, the nature of which will become more apparent, the invention will be more fully understood by reference to the drawings, the accompanying detailed description and the appended claims.

The invention consists of certain novel features and structural details hereinafter fully described, illustrated in the accompanying drawings, and particularly pointed in the appended claims, it being understood that various changes in the details may be made without departing from the spirit, or sacrificing any of the advantages of the present invention.

DESCRIPTION OF THE DRAWINGS

For the purpose of facilitating and understanding the invention, there is illustrated in the accompanying drawings a preferred embodiment thereof, from an inspection of which, when considered in connection with the following description, the invention, its construction and operation, and many of its advantages will be readily understood and appreciated.

FIG. 1 is a side view of a localization needle assembly provided by the present invention;

FIG. 2 is an enlarged side view of an inner needle structure of the localization needle assembly shown in FIG. 1;

FIG. 3 is an enlarged side view of a further embodiment of an inner needle structure for a localization needle assembly provided by the present invention;

FIG. 4 is an enlarged side view of another embodiment of an inner needle structure of a localization needle assembly;

FIGS. 5-8 are cross-sectional views for various embodiments of the needle structure illustrated in FIGS. 2 and 3;

FIG. 9 is a side view of an outer cannula of the localization needle assembly shown in FIG. 1;

FIG. 10 is a side view of the localization needle assembly provided by the present invention with the anchoring barb illustrated in its retracted position;

FIG. 10A is an enlarged fragmentary view of the distal end of the localization needle assembly illustrated in FIG. 10;

FIG. 11 is a side view of the localization needle assembly of FIG. 10, but illustrated with the anchoring barb deployed; and FIG. 11A is an enlarged fragmentary view of the distal end of the localization needle assembly of FIG. 11.

DESCRIPTION OF PREFERRED EMBODIMENTS

Referring to FIG. 1, there is illustrated a localization needle assembly 10 provided in accordance with the present invention for use in locating lesions within body tissue, and in particular for use as a breast localization needle assembly for locating nonpalpable lesions within the breast. Although the localization needle assembly 10 is specifically described with reference to an application as a breast localization assembly, the localization needle assembly 10 of the present invention has application in locating cancerous nonpalpable lesions within the human or animal body, be it a brain tumor, or any medical procedure which requires the pinpointing of a lesion, foreign body or normal structure within the body or organ of the body.

The localization needle assembly 10 includes a tubular outer cannula 11 and a needle structure 12 which is adapted for sliding movement within the outer cannula 11. The needle structure 12 defines a retractable barb 13, shown deployed in FIG. 1, whereby the barb 13 projects outward through an aperture 14 in the outer cannula 11 for anchoring the localization needle assembly to body tissue as will be described hereinafter. The barb 13 is retracted within the outer cannula 11 during introduction of the needle guide assembly into the patient's body during localization procedures, and is deployed by withdrawing the wire structure by pulling on its proximal end for immobilizing the needle during mammography.

The needle structure 12 has markings 29 and 29a thereon to provide an indication to the user as to the location of the tip and barb relative to the tip and aperture (FIG. 1) of the cannula 11. The markings enable the surgeon to know when the barb is retracted and when it is deployed. For example, marking 29 when aligned with the proximal edge 11a of the cannula indicates that the barb is retracted within the cannula 11. The marking 29a, when aligned with the proximal edge 11a of the cannula 11, indicates that the barb is fully deployed.

Referring to FIG. 2, the needle structure 12 has a proximal end 14 and a distal end 15. The needle structure 12 is formed of an elongated single wire 16 which is reinforced over a portion of its length with multiple wire strands 17 to form a unitary needle wire structure. As illustrated in FIG. 2, for example, the outer wires 17 may be wound (or stranded) in helical fashion around the core wire 16, but terminate short of the distal end of the core wire 16, defining a junction point 18 at which point the outer wires 17 are connected or secured to the core wire 16 in a suitable manner such as by solder. A further solder joint 19 is provided at the tip of the needle structure 11 at the proximal end 14 thereof. These solder connections protect the wire 11 from fraying at the proximal end 14 and at the junction 16.

The distal tip portion of the core wire 16 is bent over on itself and tightened, as is known in the art, to form the barb portion 13 which projects rearwardly from the distal tip, that is, toward the right in FIG. 2, and terminates in a sharp tip or point 20. The overbend may be secured as by solder 20a. The use of reinforcement permits the needle structure 12 to be made of a smaller diameter wire to enhance the flexibility and pliability of the needle structure without compromising its resistance to accidental transection.

For the needle structure 12 illustrated in FIG. 2, the reinforcement is provided by the multiple wire strands 17 which may be wound or stranded on the core wire 16 over a portion of its length. The outer wires 17 may be wrapped on the core wire 16 and/or may be braided before being combined with the core wire. Moreover, although wires of circular cross-section are illustrated, the outer wire or wires could be in the form of a flat band or strip having a rectangular cross-section. Also, although the core wire 16 illustrated in FIG. 2 is a single wire element, the core wire may comprise a two element structure 30 such as that illustrated in FIG. 3 wherein an inner cannula 33 is secured to the distal end of the core wire 16 as will be described. Further, as illustrated in FIG. 4, the reinforcement for a needle structure 40 is provided by coiling the core wire over a portion of its length as will hereinafter be described.

The stranded needle structures 12 and 30 illustrated in FIGS. 2 and 3 may take various forms. Referring to FIG. 5, by way of example, the needle wire structure 12 may comprise a core wire 16 on which may be wound or stranded a plurality of outer wires 17, there being twelve wires 17 illustrated in FIG. 5.

Referring to FIG. 6, in a further embodiment, the needle structure 12a includes twelve outer wires 22 wrapped around six intermediate wires 23 wrapped around a single core wire 16. In FIG. 7, a needle structure 12b includes a single core wire 16 upon which are wrapped six strands 24 each including seven wires 25. In another embodiment for a wire structure 12c shown in FIG. 8, the core 16' comprises a stranded wire including three wires 27 upon which are wound or stranded nine outer wires 28.

The stranded configuration for the needle structure 12 provides reinforcement for the needle structure along substantially its entire length providing many advantages over a conventional wire needle. For example, multiple strands resist accidental transection. Even if several strands were to be cut, functionality of the needle structure would be preserved. Also, strands are more flexible than stiff single wires and the use of strands reduces risk of additional penetration of organs or vessels or migration within cavity due to accidental contact with the needle assembly during normal movement of the patient during diagnostic procedures as during the transportation of the patient to surgery. The flexibility and pliability allow easier handling of the wire structure outside of the patient's body and fastening of the wire structure to the patient's skin with adhesive tape. Moreover, a larger strand has greater tensile strength than a single small diameter wire, and a strand resist fatigue breakage better than does a single wire.

Referring to FIG. 3, there is illustrated a further embodiment for a stranded needle structure 30 having a proximal end 31 and a distal end 32 and which includes a short inner cannula member 33 which is attached to the core wire 16 at its end 35. The needle structure 30 further includes a short wire member 36, the forward end 36a of which is secured to the inner cannula member 33 by soldering, welding, by adhesive or by mechanical means, such as, crimping, threading or shrinking. The short wire member 36 includes a free end 37 defining a barb or hook which is adapted to anchor the needle within body tissue.

Referring to FIG. 4, a further embodiment of a needle structure 40 includes a linear portion 41 at its distal end 42 and a helical portion 43 intermediate its proximal end 44 and its distal end 42, and preferably extending all the way to its proximal end. The needle structure 40 may be formed of a single wire or monofilament which is coiled from the linear portion 43 to its proximal end. The tip of the wire is folded back upon itself to define a rearwardly projecting barb 45.

The helical coiled portion 43 defines the reinforcement for the needle structure 40 while permitting use of a single wire or monofilament. This configuration provides a degree of rigidity of the needle structure in the distal end portion, permitting the barb to anchor the localization needle assembly to body tissue, and with the proximal end portion or helical coiled portion 43 providing flexibility and pliability in the portion of the structure by which the user directs the anchoring distal end to the target.

Referring to FIG. 9, the outer cannula 11 includes a hollow tubular shaft portion 51 having a proximal end 52 and a distal end 53. The cannula may be comprised of a rigid material composed of either steel, polymer or a combination thereof and may be of a variable length as required. A hub 54 is mounted on the proximal end of the shaft 51 to facilitate use of the cannula. The distal end 53 is provided with a sharp point 55. The tubular shaft 51 has an opening 14 formed therethrough at a predetermined distance from the tip 55 of the cannula. Markings 58 are provided on the outer surface of the cannula 11 to provide an indication to the surgeon of the depth to which the cannula has been inserted into the body of the patient being treated.

The use of the needle guide assembly provided by the present invention is described with reference to an embodiment for the needle guide assembly 60 illustrated in FIGS. 10 and 11 which includes the needle structure 30 illustrated in FIG. 3 and the outer cannula 11 illustrated in FIG. 7. However, the needle structures 12 and 40 illustrated in FIGS. 2 and 4, would function in a similar manner in localization procedures.

Referring to FIGS. 10 and 10A, there is illustrated a needle guide assembly 60 which includes the needle structure 30 assembled with the cannula 11. In FIGS. 10 and 10A, the barb 36 is illustrated in the retracted position. In the retracted position, the barb 36 is located within the bore 57 forward of the opening 14 with the barb 36 engaging the inner wall 59 of the tubular shaft 51.

Referring to FIGS. 11 and 11A, the needle guide assembly 60 is illustrated with the barb 36 in the extended position wherein the needle wire structure 30 has withdrawn back into the cannula 11, moving the inner cannula 33 towards the right in FIGS. 11 and 11A, permitting the barb 36 to pass through the opening 14 in the cannula 11 for deployment.

In use, referring to FIGS. 10 and 10A, initially, the needle structure 30 is positioned within cannula 11 so that the tip of the needle structure 30 extends outwardly of the cannula 11 at the distal end 55 of the cannula 11 such that the barb 36 is retracted during insertion of the assembly into the tissue of the body.

The localization needle assembly 60 is advanced to the target area of a human or animal body, either for simply marking the location, be it the breast, liver, ductal structure, brain, lung or other organs where it is desirable to take a biopsy, a sample structure or to surgically remove an unwanted mass or lesion from the body. The desired position is obtained by advancing the needle assembly into the target area using the forward pressure on the hub on the cannula 11 to advance the localization needle assembly 60 into the target. After the needle has been properly positioned using either X-ray, ultrasound, or other filming means, the inner needle assembly 30 is withdrawn back into the cannula thereby deploying the barb member 36 through opening 14 in the sidewall of the cannula 11 to lock and firmly anchor the localization needle assembly 60 in position within the body tissue, immobilizing the assembly 60. When the localization needle assembly 60 has been inserted into the breast, the movement of the barb member 36 into the body tissue anchors and firmly retains the needle assembly within the breast or body tissue. The opening 14 may be located on the outer cannula at a position where it is desired that the needle assembly be anchored to the body tissue. Preferably this position is adjacent the distal end, but it could be located at any position intermediate the distal and proximal ends provided proper anchoring of the localization needle assembly occurs with respect to the body tissue.

If after deployment of the barb 36, it is determined by X-ray, ultrasound or filming means, that the localization needle assembly has not located a lesion, the barb 36 can be retracted by advancing the stranded needle and the inner cannula attached thereto into the outer cannula 11. The localization needle assembly 60 can then be repositioned to locate the lesion, the inner cannula 33 being moved outwardly of the outer cannula 11 to again deploy the barb 36 when the lesion is located.

As is well known in the art, the length of the outer cannula can vary depending upon the depth of the lesion that is to be localized and identified for subsequent surgical operation.

I claim:

1. A localization needle assembly for pinpointing lesions within body tissue, including in combination:
    an outer tubular cannula member having a distal end and a proximal end with said cannula member having an opening predeterminedly located from said distal end,
    an elongated inner needle structure having a distal end and a proximal end, with a linear portion at its distal end and a flexible reinforced portion extending proximal from said linear portion towards its proximal end, said needle structure comprising an elongated wire core means and said flexible reinforced portion comprising multiple wire strands wound on said wire core means over a portion of its length, said reinforced potion terminating short of the distal end of said wire needle structure, defining said linear portion of said wire needle structure, said linear portion of said needle structure having anchoring means including an extendable and retractable barb, said inner needle structure being slidably mounted for movement within said outer cannula member between a first position and a second position, said barb being contained within said outer cannula member, extending towards said opening in said outer cannula member when said needle structure is in said first position and said barb being moved outward of said outer cannula member through said opening predeterminedly located from the distal end of said outer cannula member to engage body tissue when said needle structure is moved to said second position to anchor the localization needle assembly to body tissue.

2. A localization needle assembly according to claim 1, wherein said wire core means of said needle structure comprises an elongated single core wire, said multiple wire strands being wound on said core wire over a portion of its length to form a unitary wire needle structure.

3. A localization needle assembly according to claim 2, wherein said multiple wire strands comprise a first layer of wires helically wound on said core wire and a second layer of wires helically wound on said first layer of wires.

4. A localization needle assembly according to claim 2, wherein each of said wire strands comprises a core wire having a plurality of wires helically wound therein.

5. A localization needle assembly according to claim 1, wherein said anchoring means comprises a hollow generally cylindrical inner cannula secured to said linear portion of said needle structure and adapted to be received within said outer cannula member for sliding movement therewithin, said barb comprising a segment of wire having a fixed end secured to said inner cannula and a free end projecting rearwardly of the distal end of said outer cannula member.

6. A localization needle assembly according to claim 1, wherein the tip of said linear portion is folded over upon itself with its tip portion projecting rearwardly defining said barb.

7. A localization needle assembly for pinpointing lesions within body tissue, including in combination:
an outer tubular cannula member having a distal end and a proximal end with said cannula member having an opening predeterminedly located from said distal end,
an elongated single wire needle with multiple wire strands wound thereon over a portion of its length to form a unitary wire needle structure having a distal end and a proximal end with a flexible reinforced portion, said reinforced portion terminating short of said distal end of said needle structure defining a linear portion for said needle wire structure at its distal end, said needle structure having anchoring means including an extendable and retractable barb portion at its distal end, said needle structure being slidably mounted for movement within said outer cannula member between a first position and a second position, said barb portion extending towards said opening in said outer cannula member when said needle structure is in said first position and said barb portion being moved outward of said outer cannula member through said opening predeterminedly located from the distal end of said outer cannula member to engage body tissue when said needle structure is moved to said second position to anchor the localization needle assembly to body tissue.

8. A localization needle assembly according to claim 7, wherein needle structure comprises a core wire and a plurality of outer wires helically wound around said core wire.

9. A localization needle assembly according to claim 8, wherein said plurality of outer wires comprise a first layer of wires helically wound on said core wire and a second layer of wires helically wound on said first layer of wires.

10. A localization needle assembly according to claim 8, wherein each of said outer wires comprise a stranded wire including a core wire having a plurality of wires helically wound thereon.

11. A localization needle assembly according to claim 8, wherein the tip of said core wire is folded over upon itself with its pointed tip portion projecting rearwardly defining said barb portion.

12. A localization needle assembly according to claim 11, wherein said folded over portion defines a blunt forward end for said needle structure, and includes means securing said folded over portion.

13. A localization needle assembly according to claim 7, wherein said needle structure comprises a stranded core wire including a plurality of wires wound together to form a unitary core wire structure and a plurality of outer wires helically wound around said stranded core wire.

14. A localization needle assembly for pinpointing lesions within body tissue, including in combination:
an outer tubular cannula member having a distal end and a proximal end with said cannula member having an opening predeterminedly located from said distal end,
an elongated needle structure including a wire core means reinforced over a portion of its length with multiple wire strands to form a unitary wire needle structure having a distal end portion and a proximal end portion, said needle structure having anchoring means at its distal end portion, said needle being slidably mounted for movement within said outer cannula member between an extended position and a retracted position, and
said anchoring means having a mounting portion secured to said distal end portion of said needle structure and a barb portion carried by said mounting portion and extending towards said opening in said outer cannula member when said needle structure is in its extended position and said barb portion being moved outward of said outer cannula member through said opening predeterminedly located from the distal end of said outer cannula member to engage body tissue when said needle structure is moved to its retracted position to anchor the localization needle assembly to body tissue.

15. A localization needle assembly according to claim 14, wherein said wire core means of said needle structure comprises an elongated single core wire and wherein said multiple wire strands are wound on said core wire over a portion of its length to form said unitary wire needle structure.

16. A localization needle assembly according to claim 15, wherein said multiple wire strands comprise a first layer of wires helically wound on said core wire and a second layer of wires helically wound on said first layer of wires.

17. A localization needle assembly according to claim 13, wherein each of said wire strands comprises a core wire having a plurality of wires helically wound therein.

18. A localization needle assembly for pinpointing lesions within body tissue, including in combination:
   an outer tubular cannula member having a distal end and a proximal end with said cannula member having an opening predeterminedly located from said distal end,
   an elongated needle structure including a core wire with multiple wire strands wound thereon over a portion of its length to form a unitary wire needle structure having a distal end and a proximal end with a flexible reinforced portion, said flexible reinforced portion terminating short of said distal end of said needle structure defining a linear portion for said wire needle structure at its distal end, said core wire having a sharp tip portion which is folded over defining a blunt nose portion and a sharp extendable and retractable barb portion which extends rearwardly from the blunt nose portion at the distal end of said needle structure, the length of said needle structure being greater than the length of said outer cannula member and a portion of the flexible reinforced portion of the proximal end of said needle structure extending beyond the proximal end of said outer cannula member, said needle structure being slidably mounted for movement within said outer cannula member between a first position and a second position, and
   said barb portion extending towards said opening in said outer cannula member when said needle structure is in said first position and said barb portion being moved outward of said outer cannula member through said opening predeterminedly located from the distal end of said outer cannula member to engage body tissue when said needle structure is moved to said second position to anchor the localization needle assembly to body tissue.

19. A surgical needle comprising:
   an elongated needle structure having a distal end and a proximal end, with a linear portion at its distal end and a flexible reinforced portion extending from said linear portion towards its proximal end, said needle structure comprising an elongated wire core means and said flexible reinforced portion comprising multiple wire strands wound on said wire core means over a portion of its length defining said flexible reinforced portion, said reinforced portion terminating short of said distal end, defining said linear portion of said wire needle structure, said linear portion of said needle structure having anchoring means including a barb adapted to engage body tissue to anchor the needle structure to body tissue.

20. A surgical needle according to claim 19, wherein said multiple wire strands comprise a first layer of wires helically wound on said wire core means and a second layer of wires helically wound on said first layer of wires.

21. A surgical needle according to claim 19, wherein each of said wire strands comprises a core wire having a plurality of wires helically wound therein.

22. A surgical needle according to claim 19, wherein said anchoring means comprises a hollow generally cylindrical cannula secured to said linear portion of said needle structure, and whereas said barb comprises a segment of wire having a fixed end secured to said cannula and a free end projecting outwardly from said cannula.

23. A surgical needle according to claim 19, wherein the tip of said linear portion is folded over upon itself with its tip portion projecting rearwardly defining said barb.

24. A surgical needle comprising:
   an elongated single wire needle reinforced over a portion of its length with multiple wire strands to form a unitary wire needle structure having a distal end and a proximal end with a flexible reinforced portion, said reinforced portion terminating short of said distal end, defining a linear portion for said needle structure at its distal end, said linear portion of said needle structure having anchoring means including a barb portion adapted to engage body tissue to anchor the needle structure to body tissue.

25. A localization needle assembly for pinpointing lesions within body tissue, including in combination:
   an outer tubular cannula member having a distal end and a proximal end with said cannula member having an opening predeterminedly located from said distal end,
   an elongated single wire needle reinforced over a portion of its length with multiple wire strands to form a unitary wire needle structure having a distal end portion and a proximal end portion, and anchoring means including a hollow generally cylindrical inner cannula secured to said distal end portion of said needle structure and adapted to be received within said outer cannula member, and a barb portion comprising a segment of wire having a fixed end secured to said inner cannula and a free end projecting rearwardly of the distal end of said outer cannula member, said needle structure and said anchoring means being mounted within said outer cannula member for sliding movement therewithin between a first position and a second position, said barb portion extending towards said opening in said outer cannula member when said needle structure is in said first position and said barb portion being moved outward of said outer cannula member through said opening predeterminedly located from the distal end of said outer cannula member to engage body tissue when said needle structure is moved to said second position to anchor the localization needle assembly to body tissue.

26. A localization needle assembly according to claim 25, wherein said inner cannula has a proximal end and a distal end with an axial passageway therethrough, said needle structure having a core portion secured to the proximal end of said inner cannula and said inner cannula having a sidewall with an aperture therethrough, said wire segment having its fixed end located in said passageway and secured to said inner cannula therewithin and having its free end extending through said aperture.

27. A localization needle assembly for pinpointing lesions within body tissue, including in combination:
   an outer tubular cannula member having a distal end and a proximal end with said cannula member having an opening predeterminedly located from said distal end,
   an elongated inner needle having a distal end and a proximal end, with a linear portion at its distal end and a flexible reinforced portion extending from said linear portion toward its proximal end, said needle including a single monofilament which is helically coiled along a portion of its length, defining said flexible reinforced portion, and straight at its distal end, defining said linear portion, said linear portion of said inner needle having anchoring means including an extendable and retractable barb, said inner needle being slidably mounted for movement within said outer cannula member between a first position and a second position, said barb being contained within said outer cannula member, extending towards said opening in said outer cannula member when said inner needle is in said first position and said barb being moved outward of said outer cannula member through said opening predeterminedly located from the distal end of said outer cannula member to engage body tissue when said inner needle is moved to said second position to anchor the localization needle assembly to body tissue.

28. A surgical needle comprising:
   an elongated single monofilament having a distal end and a proximal end, with a linear portion at its distal end and a flexible reinforced portion extending from said linear portion toward its proximal end, said monofilament being helically coiled along a portion of its length defining said flexible reinforced portion, and straight at its distal end defining said linear portion, said linear portion having anchoring means including a barb adapted to engage body tissue to anchor said monofilament to body tissue.

* * * * *